United States Patent [19]

Chan et al.

[11] Patent Number: 5,233,156
[45] Date of Patent: Aug. 3, 1993

[54] HIGH SOLIDS CONTENT SAMPLE TORCHES AND METHOD OF USE

[75] Inventors: Shi-Kit Chan; Sidney L. Geil, both of Omaha, Nebr.

[73] Assignee: Cetac Technologies Inc., Omaha, Nebr.

[21] Appl. No.: 750,976

[22] Filed: Aug. 28, 1991

[51] Int. Cl.$^5$ ............................................... B23K 9/00
[52] U.S. Cl. ......................... 219/121.52; 219/121.54; 219/121.5; 219/121.59; 315/111.51
[58] Field of Search ........................ 219/121.52, 121.48, 219/121.51, 121.49, 75, 121.59; 315/111.51, 111.21

[56] References Cited

U.S. PATENT DOCUMENTS

| Re. 29,304 | 7/1977 | Greenfield et al. | |
| 3,467,471 | 9/1969 | Greenfield et al. | 219/121.48 X |
| 4,266,113 | 5/1981 | Denton et al. | 219/121 PQ |
| 4,271,100 | 6/1981 | Trassy . | |
| 4,431,901 | 2/1984 | Hull | 219/121 PR |
| 4,482,246 | 4/1988 | Myer et al. | 356/316 |
| 4,551,609 | 11/1985 | Falk | 219/121 PR |
| 4,575,609 | 3/1986 | Fassel et al. | 219/121 PY |
| 4,578,560 | 3/1986 | Tanaka et al. | 219/121 PR |
| 4,739,147 | 11/1984 | Meyer et al. . | |
| 4,794,230 | 12/1988 | Seliskar et al. | 219/121.52 |
| 4,833,294 | 5/1989 | Montaser et al. . | |
| 4,897,579 | 1/1990 | Hull et al. | 315/111.51 |
| 4,926,021 | 5/1990 | Streusand et al. . | |
| 4,990,740 | 2/1991 | Myer | 219/121.52 |
| 5,012,065 | 4/1991 | Rayson et al. | 219/121.52 |

FOREIGN PATENT DOCUMENTS 0052748 3/1985 Japan .
0136052 3/1985 Japan .
0210754 9/1988 Japan .
0143936 6/1989 Japan .

OTHER PUBLICATIONS

Reduction of Argon Consumption by a Water Cooled Torch in Inductively Coupled Plasma Emission Spectrometry-Kornblum et al. Analtyical Chemistry, vol. 51, No. 14 Dec. 1979.
John Yvon Application Note...JCP Analysis of Alkali Elements, The Past and the Present.

Primary Examiner—Mark H. Paschall
Attorney, Agent, or Firm—James D. Welch

[57] ABSTRACT

Torches of the type used in Inductively Coupled Plasma sample analysis systems are disclosed. The torches are designed to provide a user with the ability to minimize sample carry-over and torch clogging problems during use. The torches are suitable for use with high solids content samples prepared by ultrasonic nebulization and other high efficiency sample introduction systems. The torches incorporate means based upon design criteria which include minimization of critical tapers or constrictions in sample injecting tube and other tubes of a torch, providing means which allow control of the temperature of various components in a torch and indirectly a sample per se introduced thereto, and providing means which allow auxiliary gas flows through a torch which aid sample flow through the torch. In addition, external control of sample solvent vapor content can be practiced during an analysis procedure to further reduce any tendency of sample solids to adhere to and accumulate upon torch components.

28 Claims, 2 Drawing Sheets

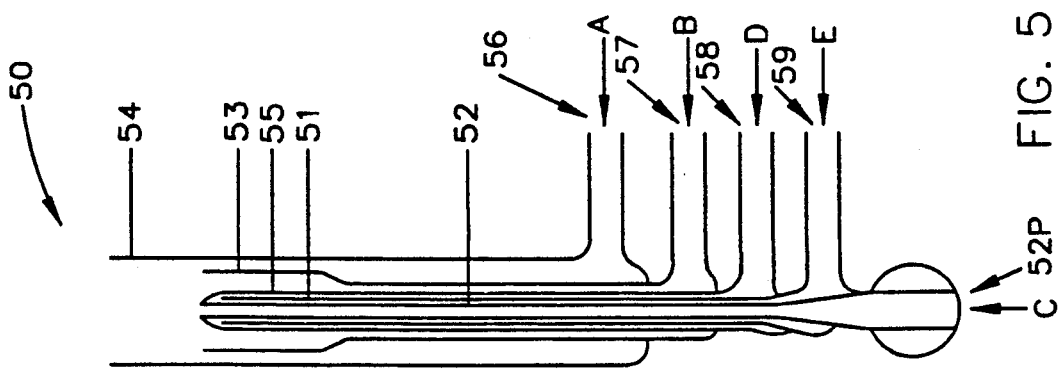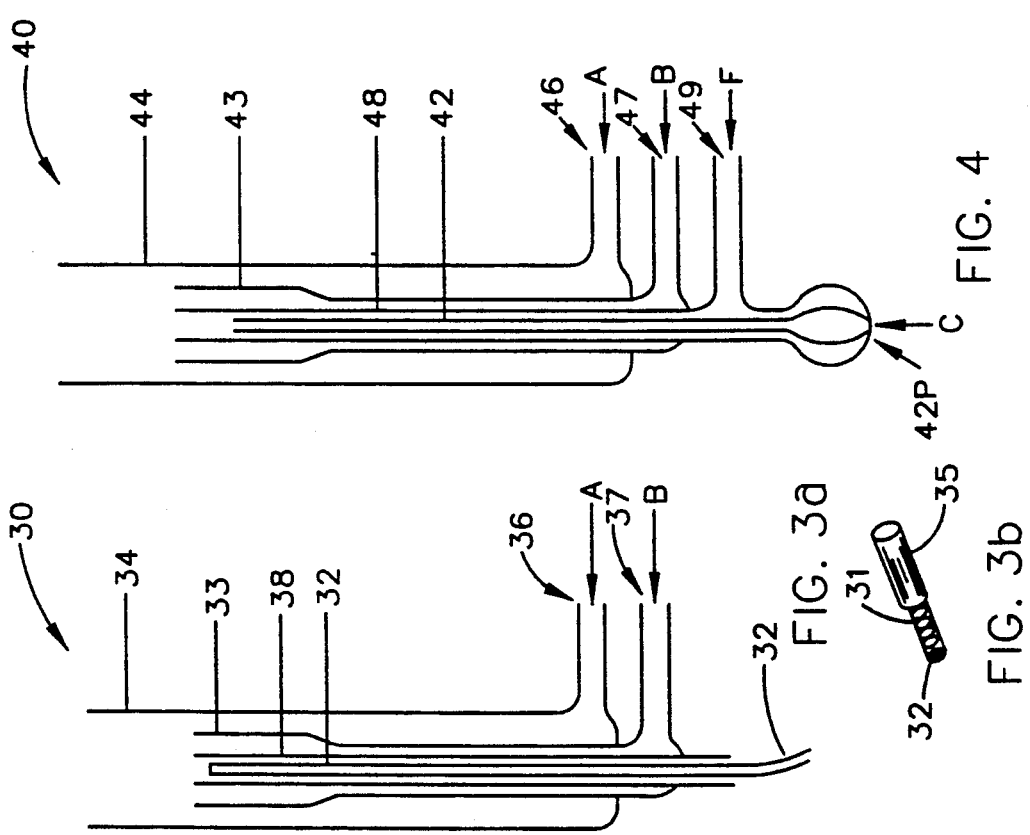

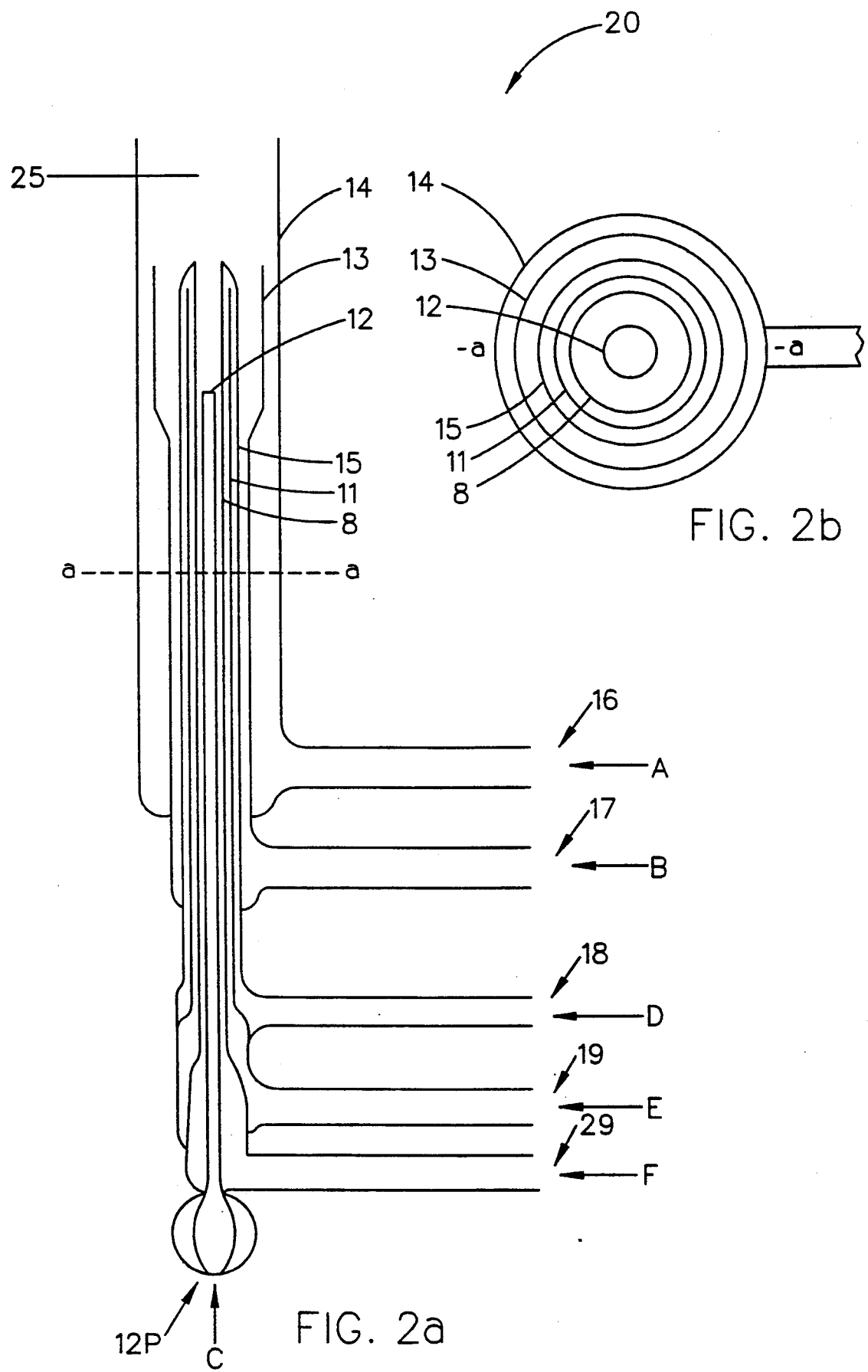

HIGH SOLIDS CONTENT SAMPLE TORCHES AND METHOD OF USE

TECHNICAL FIELD

The present invention relates to systems used for analyzing samples, and more particularly to torches of the type used with inductively coupled plasma analysis of samples, which torches are constructed to minimize sample retention and torch clogging when high solids content samples are entered thereto.

BACKGROUND

The technique of using a plasma to provide energy to atoms, ions and/or molecules in a sample introduced thereto, which atoms, ions and/or molecules interact with the energy of the plasma and become "excited" thereby, is well known. The electrons of the atoms, ions and/or molecules of a sample which interact with the energy of a plasma are caused to move from lower energy state orbitals into higher energy state orbitals of their respective atoms, ions and/or molecules. When the electrons later return to their more stable lower energy state orbitals an electromagnetic (hereinafter EM), wave radiation, is caused to be emitted. The frequency spectrum of the emitted EM wave radiation is an identifying "fingerprint" of the atoms, ions and/or molecules present in the sample. In addition, interaction of sample with the energy present in a plasma can cause sample fragments, including both positive and negative ions, to be formed. Said sample fragments can be analyzed in mass spectrometry analysis systems to provide a sample identifying mass spectrum.

To introduce a sample to a plasma it is necessary to provide a means for producing a plasma at an intended and contained location. Said location must be situated and supported so that a sample to be analyzed can be easily introduced thereto, and so that EM wave analysis equipment or a sample fragment detector can monitor the resulting emitted EM wave radiation spectra or intercept sample fragments, respectively.

The relationship between the plasma location, sample introduction and EM wave or sample fragment intercepting analysis equipments, is typically established and maintained by a "torch". Torches are typically constructed from a series of concentric quartz tubes and ports which provide access to spaces formed between outer and inner surfaces of the various concentric tubes. It is possible to use other materials, such as ceramics etc. in constructing a torch as well, hence the term "tube" will be used independently in the following.

The innermost concentric tube is typically termed a sample injector tube based upon the function with which it is associated. In standardly available torches the sample injector tube is typically of a decreasing inner diameter as the longitudinal dimension thereof is transcended from the lower aspect thereof to the upper aspect thereof as viewed in side elevation, as better described below in conjunction with other elements of a standard torch. The purpose of the decreasing inner diameter is to cause a flow of sample to increase in velocity as it transverses the sample injector tube and exits therefrom at the upper aspect thereof prior to entering a plasma, again as better described below. Continuing, the sample injector tube is typically concentrically surrounded by a second, larger inner diameter tube, typically termed an intermediate tube. The upper aspect of the intermediate tube typically, but not necessarily, extends vertically past the upper aspect of the sample injector tube, as the combination of elements is viewed in side elevation from a distance perpendicularly removed therefrom, with the longitudinal dimensions of the tubes projecting upward, perpendicularly from an underlying horizontal surface. Surrounding the concentric combination of sample injector and intermediate tubes just described, is typically a third concentric tube of an inner diameter large enough to contain the identified combination of tubes. Said larger inner diameter tube is typically termed, appropriately, the outer tube. Viewed again in side elevation and in combination with the sample injector and intermediate tubes as described above, the upper aspect of the outer tube extends to a vertical level above the more centrally located tubes. It is within the space within the outer tube, but above the upper aspects of the more centrally located tubes that a plasma is typically caused to be formed during use of the torch to analyze a sample. This is normally effected by placing an electrically conductive coil around the outer surface of the outer tube, and energizing it with an electrical current at 27 Megahertz, or at some other plasma forming frequency. The plasma formed by this technique is typically termed an "Inductively Coupled Plasma", or "ICP" for short.

At the lower aspect, viewed as described above, of the torch concentric tube combination comprising the sample injector tube, intermediate tube and outer tube there are typically ports. One such port, the intermediate port, provides access to the annular space formed between the outer surface of the sample injector tube and the inner surface of the intermediate tube; and another such access port, the outer port, provides access to the annular space formed between the outer surface of the intermediate tube and the inner surface of the outer tube. Another port, the sample flow port, provides access to the space within the sample injector tube. In use a sample is introduced to the sample injector tube via the sample flow port and is forced by a driving pressure to transverse the length of the sample injector tube vertically and eject therefrom at the upper aspect thereof into the space in which a plasma can be formed, as described above. A gas is injected into each of the outer and intermediate ports in such a manner as to cause it to flow, typically, tangentially around and upward in the space within the torch associated with each said access port. Said gas flows can be described as following a spiral and upward locus. It is also possible to inject gas into one or both of the outer and intermediate ports so that it flows vertically, in a laminar manner, rather than tangentially in the torch. The basic purpose of said tangential or vertical gas flows is to insulate the various tubes which they contact, which tubes typically melt at approximately twelve hundred (1200) degrees centigrade or below, from the heat of a plasma, the temperature of which can exceed five thousand (5,000) degrees centigrade. Another purpose of the tangentially or vertically injected gas flows is to aid with positioning the plasma in the upper aspect of the torch. As well, the gas flow introduced into the intermediate port is especially useful in helping to initially create a plasma, and the gas flow injected into the outer port is especially useful in shielding the inner surface of the outer tube in the vertically upper aspect, plasma associated region thereof, from the heat of the plasma.

It is also important, as regards the present invention, to understand how a sample is prepared for analysis.

Typically a pneumatic nebulizer is utilized. Said pneumatic nebulizer accepts a sample solution, and ejects said sample solution via a spray aperture, under pressure, to form nebulized sample solution droplets. A carrier gas flow might also be introduced to help cleave the ejected solution. A spectrum of various diameter droplets is formed by said action. The larger diameter droplets, (e.g. larger than eleven (11) microns in diameter), are drained off as they fall, typically under the influence of gravity, to a vertically lower aspect located collecting surface of an aerosol chamber of the pneumatic nebulizer system. The finer droplets, however, are entered into the sample flow port of the torch, after which they are caused to transverse the vertically oriented length of the sample injector tube and eject into the region of the torch in which a plasma can be formed. Typically said motion is caused by a pressure gradient which results from the entering of a carrier gas flow along with the sample. Analysis is performed when the sample so entered is subjected to the plasma, interacts therewith, and causes identifying EM wave radiation to be emitted, or sample fragments to be produced. EM wave detecting equipment, and/or sample fragment analysis equipment positioned to intercept the emitted EM wave radiation, or to intercept sample fragments, then develops frequency or mass spectrum information respectively, which can be used to identify the elemental and molecular components of a sample. Existing torches, as described above, work relatively well when provided a sample produced by a low efficiency nebulizer. Such a sample is properly termed a "low solids" content sample. This is the case as a large portion, (e.g. typically over ninety-eight (98%) percent), of the nebulized sample solution droplets created by a pneumatic nebulizer are of a relatively large diameter and do not enter the torch. Hence, it will be appreciated that a large portion of the solids in a sample entered into a low efficiency nebulizer, (e.g. typical pneumatic nebulizers), for nebulization is lost.

Recently, CETAC TECHNOLOGIES INC., of Omaha, Nebr. has commercialized a different type of nebulizing equipment. The descriptive term for the new nebulizing equipment is "Ultrasonic Nebulizer". Said device provides sample solution droplets which contain a far greater content of relatively small diameter droplets, (e.g. diameters less than eleven (11) microns). As a result, far more of the sample solution droplets (thirty (30) times or more as compared to the result created by a low efficiency pneumatic nebulizer), are available for entry into a torch for analysis. That is, far less of the sample solids of a sample solution are drained off in the form of relatively large droplets which never reach the torch sample flow port. This, it will be appreciated, can provide a far larger solids content nebulized sample to a torch. (This is especially the case when the solids content of a sample solution which is nebulized exceeds one-half (0.5%) to one (1%) percent thereof, thereby constituting a high solids content solution). The sample produced by the CETAC ultrasonic nebulizer is, thus, termed a "High Solids" content sample. The Ultrasonic Nebulizer, it is mentioned, provides the superior sample solids content, as compared to that provided by a pneumatic nebulizer, by using the vibrational energy which is developed by a piezoelectric crystal or equivalent, when operating as an element of an oscillating circuit. Typically, but not necessarily, such a piezoelectric crystal or equivalent and oscillator circuit will be structured so as to cause the piezoelectric crystal or equivalent to vibrate at one-and-three-tenths (1.3) Megahertz. When this frequency is used it has been found that the CETAC system provides over thirty (30) percent of sample solution droplets with a diameter of eleven (11) microns or less. In use, a solution of sample solids and a solvent are caused to impinge upon said vibrating piezoelectric crystal or equivalent, or in close proximity thereto, and thereat are instantaneously transformed into nebulized sample solution droplets. The Ultrasonic Nebulizer of CETAC TECHNOLOGIES INC. also incorporates a desolvating chamber in which the solvent is removed from the nebulized sample solution droplets, thereby providing desolvated, fine particles of sample for entry to a sample flow port of a plasma torch analysis system. By control of the desolvation process, it is noted, the solvent vapor content of the resulting high solids content nebulized sample can be controlled.

It is desirable to provide higher solids content samples to a torch, based upon less sample solids loss in the nebulizing and desolvation processes, as the sensitivity of the overall analysis equipment system is increased. However, problems have been found to exist when a typical standard torch, as described above, is used with high solids content samples. In particular, the standard typically available torches tend to be prone to retain solids from a sample introduced in one analysis procedure, and release said retained sample solids during subsequent analysis procedures. This effect is termed a "carry-over" or "memory" effect. Possibly more frustrating, however, than even the sample carrier over effect, is the torch clogging effect. That is, the entry of higher solids content samples to a sample flow port of a standard torch can lead to the standard torch actually becoming clogged by adherence to and accumulation of said sample solids on various components of the standard torch. One particularly obvious example of a component of a standard torch which is susceptable to clogging is the tapering of the sample injector tube. As discussed above, said taper is normally present to cause an increase in the ejection velocity of sample particle flow which leaves the vertically upper aspect of a sample injection tube.

A search of Patents produced no teachings which are directly on point. That is, no prior Patents were found which directly focus upon providing a torch, or torches which are specifically designed to be used with high solids content nebulized samples and which serve to minimize sample carry-over and clogging effects when used with high solids content samples. A Patent to Dorn et al. U.S. Pat. No. 4,980,057 teaches the use of an ultrasionic nebulizer in conjunction with pneumatic means to nebulize samples, and another Patent, U.S. Pat. No. 4,109,863 to Olsen et al. teaches an ultrasonic nebulizing system in which the piezoelectric or equivalent therein is secured to and encased in an enclosed, protective, hollow body. In addition, Patents which teach some interesting torch designs were found. For instance, U.S. Pat. No. 3,467,471 and U.S. Pat. No. Re. 29,304 to Greenfield et al. teach torches which provide an additional concentric tube within the sample injection tube of the standard torch. In use the additional tube carries sample and a gas jet is injected into the annular space between the outer surface of the additional tube, and the inner surface of what would be the sample injector tube were the additional tube not present. The gas jet causes a reduced pressure to develop at the vertically upper aspect of the additional tube. Said additional tube, at its vertically lower aspect, is placed into a source of sample and said sample is, by the Bernouli effect caused to flow through the additional tube. Mention is made of injecting an aerosol, (i.e. nebulized) sample into the additional tube, but such is discouraged by the Greenfield et al. teachings. The explanation given is that then known methods of preparing sample in an aerosol form causes loss of a large amount of sample. It is emphasised that this is the very problem which use of the high efficiency CETAC ultrasonic nebulizer in the present invention has overcome. As a result, certain aspects of the Greenfield et al. inventions might be found to provide a benefit, when used as described in other sections of this Disclosure, not appreciated by Greenfield et al., when said Greenfield et al. invention is considered in view of the present state of the art regarding sample nebulization techniques. In addition, Japanese Patents owned by the Shimadzu Corporation, Nos. JA 0136052, JA 0210754, JA 0052748 and JA 0143936 also teach torches with a similar geometry to that taught in the Greenfield Patents. However, if a gas is caused to flow in the space between the outer surface of the additional tube and the inner surface of what would be the sample injector tube in a standard torch, it is not caused to do so simultaneous with an aerosol form sample flow through the additional tube. One such Patent, No. JA 0136052 uses the identified gas flow as a means to allow easy extinguishing of a filament plasma. The invention in JA 0210754 uses the identified gas flow to lift a sample vapor into a plasma, which sample vapor is created near the plasma by a heating means. The invention in JA 0143936 uses said gas flow in an alternating schedule with a flow through the additional tube. Both flows include sample therein, and the torch is designed with a view to allowing easy construction of a calibration curve. A Patent to Tamaka et al. U.S. Pat. No. 4,578,560 teaches the use of concentric tubes, (termed pipes in said Patent), which can be combined to form a torch with multiple tubes present. Flanges on said tubes facilitate the combining of said tubes. Other Patents teach the use of flowing fluid to minimize overheating of a torch during use. For instance, a Patent to Rayson et al., U.S. Pat. No. 5,012,065, teaches that a gas should be directed to flow in a laminar fashion along the inner surface of the outer tube. The presence of inserts between the outer and intermediate tube provide longitudinal channels which govern said gas flow. Another Patent, U.S. Pat. No. 4,551,609 to Falk teaches that a dead space should be sealed between the lower portions of the sample injector tube (termed a capillary tube in said Patent), and the intermediate tube (termed an inner jacket in said Patent). The closing of said dead space apparently reduces the amount of cooling gas required to be entered to the equivalent of the outer port in said invention. A Patent to Seliskar et al., U.S. Pat. No. 4,794,230 also teaches an invention which provides cooling to the outer components of the torch therein. However, the cooling is provided by water which flows within an additional tubular element which surrounds the equivalent of the outer tube in said invention, over the outer surface of the equivalent of the outer tube.

A need for a torch, or torches, which are specifically designed to allow use so as to limit the tendency for sample carry over and/or torch clogging when high solids content samples are introduced thereto, is thus identified. The need has recently been rendered critical by the availability in the market of the highly efficient ultrasonic nebulizer produced and marketed by CETAC TECHNOLOGIES INC.

DISCLOSURE OF THE INVENTION

The need identified in the Background Section is met by the present invention. The present invention identifies three basic considerations, or alternatively phrased, design criteria, for torches which are to be used in the analysis of high solids content samples.

The first design criteria is that the components of a torch for use with high solids content samples should contain no, or at least minimize, critical tapers therein at which sample solids tend to accumulate as they pass through the torch. The second design criteria is that an auxiliary gas flow might be provided and be utilized to aid sample solids flow through a torch and thereby help prevent adherence to and accumulation thereof onto a component of the torch, and the third design criteria is that various components of the torch might subject to temperature control such that when a specific sample solid is present any tendency of said specific sample solid to adhere to the temperature controlled component(s) is minimized. Of course, the optimum temperature for a specific sample solid and torch tube material combination will vary with different sample solid and torch tube material combinations, hence, the important consideration is that the user be able to vary and control torch component temperatures as desired. Of importance is that the present invention serves to control sample temperture, not only torch component temperature, by way of torch component temperature control. Thus, the focus of temperature control in the present invention is different, compared to prior art inventions of which the inventor is aware. In addition, while not a torch design criteria, during use external sample solvent vapor content, or sample solvent vapor control, in addition to torch component temperature control might be practiced. As mentioned in the Background Section, the CETAC ultrasonic nebulizer provides for sample desolvation. Desolvation, however, is a relative term and adjustment of ultrasonic nebulizer desolvation operational parameters allows a spectrum of desolvated sample solvent concentrations to be achieved. Particular sample/solvent combinations can be provided to a torch to aid with minimizing sample solids adherance to torch components.

The present invention utilizes various combinations and applications of the above design criteria to arrive at a generic embodiment of a high solids content sample torch, as well as various modified embodiments thereof. It is noted that all of the high solids content sample torches taught herein have as a common element the presence of an additional tube, or tubes, as compared to a standard torch, which standard torch was described in the Background Section.

A generic embodiment of a high solids content sample torch utilizes all three of the basic design criteria. The system of the generic embodiment comprises outer and intermediate tubes just as in a standard torch. Central to the outer and intermediate tubes is also present a sample injector tube, much as is the case for a standard torch, with the exception that the sample injector tube typically has no tapers incorporated therein, and that it might be constructed to include a temperature control element such as a coil of high ohmic resistance electrical wire. It might also be easily removable from the other components of the high solids content sample torch. Also present in the generic embodiment of the high solids content sample torch is an auxiliary injector tube which concentrically surrounds the sample injector tube. Concentrically surrounding the auxiliary injector tube and merging therewith at the upper aspect thereof is an auxiliary jacket tube. (It is mentioned all references to upper and lower etc. with respect to torches in this disclosure are with reference to a side elevational view of the torch being considered, as viewed from a position perpendicularly removed from the torch, when it is resting upon an underlying a horizontal surface with the longitudinal dimensions of the tubes thereof projecting vertically, perpendicular to the underlying horizontal surface). Also present within the annular space between the outer surface of the auxiliary injector tube and the inner surface of the auxiliary jacket tube, but ending below the point at which said tubes merge at the upper aspects thereof, is a barrier tube.

Via ports, typically located at the lower aspect of the generic high solids sample content torch, various sample and gas flows can be entered. Just as in the case of a standard torch, tangential, or vertical (laminar) gas flows can be entered by way of outer and intermediate ports, into the annular spaces between the inner surface of the outer tube and the outer surface of the intermediate tube, and between the inner surface of the intermediate tube and the outer surface of the auxiliary jacket tube, (which is present in the analogically similar position to the outer surface of the sample injector tube of the standard torch), respectively, and said flows have similar purposes to the analogically similar flows already described with respect to said standard torch. Also present in the generic high solids content sample torch are two temperature gas ports termed temperature-in and temperature-out ports. The temperature-in port provides access to the annular space between the inner surface of the barrier tube and the outer surface of the auxiliary injector tube, while the temperature-out port provides access to the annular space between the inner surface of the auxiliary jacket tube and the outer surface of the barrier tube. By flowing temperature controlled fluid (eg gas or liquid), through the inverted "U" shaped annular space system accessed via the temperature-in and temperature-out ports the temperature of the auxiliary injector tube can be directly controlled. (Note that temperature controlled fluid can be flowed into either the Temperature-in or Temperature-out port and out the opposite port. The terminology is not to be interpreted to imply any limitations regarding temperature controlled fluid flow direction). Also present is a port into which a gas can be injected vertically into the annular space between the outer surface of the sample injection tube and the inner surface of the auxiliary injector tube, which port is termed the auxiliary sample flow port. The gas which enters said auxiliary sample flow port mingles with sample flow entered into the sample flow port, also present in the generic high solids sample torch, at the upper aspect of the sample injector tube. Said sample injector tube typically has an upper aspect which ends vertically below the upper aspect of the auxiliary injector tube, thereby allowing interaction between the sample and the auxiliary sample gas prior to being projected into the upper aspects of the torch whereat a plasma can be created for use in sample analysis. It is noted that the temperature of the auxiliary sample gas flow can also be controlled to help control the temperature of the sample injector tube during use. It is also mentioned that the sample injector port is provided sample flow which is produced by, typically, a high solids content sample flow source, such as a high efficiency ultrasonic nebulizer.

A modification of the generic embodiment of a high solids content sample torch described above is comprised of outer and intermediate tubes, oriented as described with respect to the standard and generic high solids content sample torch. Central to the intermediate tube is a modified auxiliary sample flow tube termed a support tube. The upper aspects of the support tube and the intermediate tubes are typically at approximately equal vertical levels as the torch is viewed in side elevation, as described above with respect to the generic high solids content sample torch. The vertically upper aspect of the outer tube projects considerably higher than do the upper aspects of the intermediate and support tubes, however, to provide an encompassed area in which a plasma can be created. At the lower aspect of the first modified embodiment are ports which allow access to the annular spaces formed between the various elements just described. An outer port provides access to the annular space between the inner surface of the outer tube and the outer surface of the intermediate tube. A tangential, or vertical, gas flow can be injected at this port for reasons similar to those described for the analogically similar tangential gas flow for the generic embodiment. An intermediate port provides access to the annular space formed between the inner surface of the intermediate tube and the outer surface of the support tube. Again, a tangential, or vertical gas flow can be entered to this port for reasons similar to those described for entering an analogically similar tangential gas flow into the intermediate port of the generic embodiment. Note however, that the generic embodiment analogically similar annular space is bordered by the outer surface of the auxiliary jacket tube rather than that of a support tube as is the case in the first modified embodiment of the present invention. The support tube is accessed by way of an open end at the lower aspect thereof. In use a tube which carries sample, the sample injector tube, is simply slid into the space within the support tube so that the end of said sample injector tube which first enters the support port is vertically situated near the upper aspect of the support and intermediate tubes. The sample injector tube can also be fitted with a temperature controlling element along its length, such as a coil of high ohmic resistance electrical wire. During use, said temperature controlling element can be used to control the temperature of the sample injector tube. Said sample injector tube might also be covered by a strength enhancing sleeve tube.

The second modified embodiment is very similar to the first, as regards the upper extent of the torch. An outer tube concentrically surrounds an intermediate tube, which intermediate tube concentrically surrounds a tube similar to the support tube, but termed in this case, an auxiliary injector tube. The sample injector tube is concentrically surrounded by said auxiliary injector tube and the vertically upper aspect of said sample injector tube typically is positioned below the vertically upper aspect of the auxiliary injector tube. As before the terms upper and lower are taken with respect to a side elevational view as already described for other embodiments of the invention. The intermediate and auxiliary injector tubes typically have relatively equal vertical upper aspect levels, and the upper aspect of the outer tube, again, is vertically higher than the upper aspects of the other tubes of the system to provide a space in which a plasma can be formed. The major difference of the second modified embodiment as compared to the first modified embodiment is found at the lower aspect of the torch. While the first modified embodiment provides a support tube into which a separate sample injector tube is placed during use, the second modified embodiment provides a port by which access to the space inside a fixed sample injector tube can be accessed. There are also three other ports present. Two of the ports are similar to the outer and intermediate ports discussed with respect to the generic and first modified embodiments. The tangential, or vertical gas flows which are entered into said ports also have purposes and characteristics similar to the analogically similar flows in the generic and first modified embodiments. The third port is similar to the auxiliary sample flow port in the generic embodiment. A gas can be entered into said port, vertically, so that it can mingle with the sample which exits the sample injector tube at the upper aspect thereof, prior to entering the upper aspect of the torch wherein a plasma can be created and used to analyze the sample contents. The vertically injected gas helps to sweep the sample flow upward, and may also be used to help control the temperature of the sample injector tube and sample per se during use, as well.

It is noted at this point that neither of the first or second modified embodiemnts typically involves any critical tapers in the sample injector tube. The generic embodiment and the third modified (discussed below), embodiments might utilize a taper at the upper aspect of the sample injector tube however. The reason a taper is provided in a standard torch is to increase the velocity of a sample leaving the upper aspect of a sample injector tube. In the first modified embodiment the sample injector tube is a separate tube which is slid into a support tube of the first modified embodiment torch. In the second embodiment there is provided a vertically projected gas flow through the space between the inner surface of the auxiliary injector tube and the outer surface of the stationary sample injector tube which vertical gas flow aids the sample flow as it leaves the sample injector tube. A similar vertical gas flow is possible in the generic embodiment. The third modified embodiment also provides an auxiliary jacket tube which merges with the outer surface of the auxiliary sample injector tube at the upper aspects thereof, but has no provision for providing a vertical gas flow to mix with an ejected sample flow at the upper aspect of the sample injector tube, as just alluded to and which is present in the generic and second modified embodiments of the present invention. As a result, the third embodiment, in particular, might provide a bit of a taper at the upper aspect of the sample injector tube, to help increase the velocity of sample flow as it leaves the sample injector tube thereof.

The third modified embodiment of the present invention again provides the outer and intermediate tubes common in all the embodiments, and in addition includes the auxiliary injector tube and auxiliary jacket and barrier tubes as described with respect to the generic embodiment of the present invention. Also present are outer and intermediate ports and temperature-in and temperature-out ports along with the sample flow port. The purposes of the various components are the same as for their analogical counterparts found in the generic embodiment. In fact, the third modified embodiment is nearly identical to the generic embodiment except that the auxiliary sample flow port for entering vertical gas flow into the annular space between the inner surface of the auxiliary injector tube and the outer surface of the sample injector tube is not present and said space is not accessible.

It is interesting to also note that the vertically upper aspect of the sample injector tube in the generic and second modified embodiments is typically located below the vertically upper aspect of the auxiliary injector tube. The vertically upper aspect of the sample injector tube in the first modified embodiment can be adjusted in location by a user simply extending the sample injector tube further into the support tube thereof. However, in the third modified embodiment of the present invention, the vertically upper aspect of the sample injector tube is typically located at a level essentially equal to the vertically upper aspect of the intermediate tube.

The various embodiments of the present invention just described will be better understood by reference to the Detailed Description Section herein, and the accompanying drawings.

Other embodiments of the present invention can be developed by varying certain aspects of the embodiments described above in a manner similar to that by which the various modified embodiments were arrived using the generic embodiment as a starting point, and are within the scope of the present invention.

SUMMARY OF THE INVENTION

Sample analysis by means of injecting a nebulized sample into a plasma and monitoring the electromagnetic wave radiation and/or sample fragment mass spectrums of the results of interaction are well known. Also well known are standard torches which provide means which serve to physically orient a plasma location and sample introduction thereto.

Recently, a new more efficient, and market successful, means of sample nebulization, (e.g. Ultrasonic Nebulizer by CETAC TECHNOLOGIES INC.), has become commercially available. The new sample nebulizing means utilizes a piezoelectric crystal or equivalent which is caused to vibrate at, typically, one-and-three-tenths (1.3) Megahertz. A sample solution is impinged upon, or in close proximity to, the vibrating piezoelectric crystal or equivalent and the result is formation of nebulized sample solution droplets which comprise a far greater, (thirty (30) or more fold), number of fine particles than result from use of other sample nebulization means, (e.g. low efficiency pneumatic nebulizer). The higher concentration of finer nebulized sample solution droplets means that less of the sample entered to the "high efficiency" ultrasonic nebulizer is lost in the form of relatively large diameter droplets which exit the system, typically under the influence of gravity, and cannot be entered to a plasma for analysis. As a result the sensitivity of an overall sample analysis system using a high efficiency ultrasonic sample nebulizer, as compared to systems which use other types of sample nebulizers, is greatly increased.

While the ultrasonic sample nebulizer provides an efficiency advantage over other sample nebulizing means, when a sample prepared thereby is introduced to a standard torch commonly used with samples nebulized by other nebulizing means in, for instance Inductively Coupled Plasma (ICP) analysis systems, problems are found to develop. The higher sample solids content of the so prepared nebulized sample tends to cause sample carry-over and even torch clogging during use. The sample carry-over effect can adversely effect analysis results by retaining sample solids introduced during one analysis procedure in the torch, and releasing them during a subsequent analysis procedure. The clogging effect can, obviously, completely interrupt an analysis procedure.

It is the teachings of the present invention that sample solids retention in a torch can be minimized by proper design and use of the torch. Factors such as eliminating, or at least minimizing, critical tapers therein, providing the capability to a user to control the temperature of various components thereof, (and indirectly a sample per se.), during use and providing additional gas flows to aid sample solids transport through a torch are disclosed as important torch design criteria. In addition, the present invention suggests the external control of sample solvent vapor content during use, alone or in addition to use of torch design criteria effected parameter control means, as an additional means to minimize sample adherence to torch components.

The present invention then, provides torches which can be used with high solids content samples, which torches demonstrate reduced tendency toward sample carry-over and clogging problems in use.

It is therefore a primary purpose of the present invention to teach torches of the type used in ICP sample analysis, the design of which torches provides means by which to minimize sample carry-over and clogging effects therein when said torches are used to analyze high solids content samples, such as those produced by high efficiency ultrasonic sample nebulization means.

BRIEF DESCRIPTION OF THE DRAWINGS

FIG. 1a shows a side elevational view of a standard torch as viewed from a position perpendicularly removed therefrom.

FIG. 1b shows a top view of the standard torch shown in FIG. 1a.

FIG. 2a shows a side elevational view of a generic high solids sample torch as viewed from a position perpendicularly removed therefrom.

FIG. 2b shows a cross-sectional view of the generic high solids torch in FIG. 2a as viewed from thereabove. The scale of the view is expanded to better identify element relationships.

FIG. 3a shows a side elevational view of a first modified embodiment of a high solids sample torch as viewed from a position perpendicularly removed therefrom.

FIG. 3b shows a perspective view of a portion of a sample injector tube used with the high solids sample torch shown in FIG. 3a, which sample injector tube has an ohmic high resistance electrical coil and an insulator wrapped therearound.

FIG. 4 shows a side elevational view of a second modified embodiment of a high solids sample torch as viewed from a position perpendicularly removed therefrom.

FIG. 5 shows a side elevational view of a third modified embodiment of a high solids sample torch as viewed from a position perpendicularly removed therefrom.

DETAILED DESCRIPTION

Torches such as those used in Inductively Coupled Plasma (ICP), sample analysis for instance are constructed, typically, from a series of concentric quartz, or ceramic etc. tubes, (here-in-after referred to as simply tubes). See FIG. 1 for a representation of typical sample analysis torch construction (10). In use, a flow of sample (C), to be analyzed is injected into the torch at the sample flow port (2P) at the lower aspect of a sample injector tube (2), shown in FIG. 1 as the most centrally located concentric tube. Typical torches also provide for the injection of gas into other aspects of the torch. Typically argon is used, but use of other gases is also possible. FIG. 1, shows provision for entering two flows of gas (A) and (B). The first provides a gas flow (A) which is typically injected through outer port (6) in a manner which is typically tangential in that the flow follows a spiral-like upward locus motion path in the annular space between the inner surface of the outer tube (4) and the outer surface of the intermediate tube (3). The purpose of said tangential gas flow being primarily to prevent the heat developed from the establishment and maintenance of a plasma inside the upper aspect (5) of the torch when performing sample analysis, from melting the contacted elements of the torch (10) and in particular the outer tube (4) thereof at its uppermost aspect (5). A second gas flow (B) which enters intermediate port (7) is also identified and is again typically a tangential flow. The second flow (B) of gas follows a spiral-like upward locus motion path in the annular space between the outer surface of the sample injector tube (2) and the inner surface of the intermediate tube (3). This flow of gas aids with positioning the plasma in the upper aspect of the torch. (Note that gas flows "A" and "B" can also, optionally, be injected vertically into the identified annular spaces in the torch). An electrically conductive coil (not shown), is typically positioned around the outer surface of the upper portion (5) of the outer tube (4) when the torch (10) is used to analyze samples. The coil is energized by electrical currents and a plasma is inductively formed inside the upper aspect (5) of the torch as a result. Said plasma is termed an "inductively coupled plasma" or "ICP" for short. Typical energization currents at 27 Megahertz are used, although other frequencies can also be used. The sample is excited by the plasma and the resulting products of interaction, (e.g. electromagnetic wave radiation emission or sample fragments such as elements, molecules and positive and negative ions for instance), are analyzed to identify the contents of the sample.

It is of particular interest to note that the torch (10) shown in FIG. 1. shows a sample injector tube (2) which tapers (2T) as it is transversed from the lower aspect thereof toward the vertically upper aspect thereof. The purpose of the taper is to cause sample flow (C) carried within the sample injector tube (2) to increase in velocity as it readies to eject into a plasma, for instance, which plasma is utilized in sample analysis and is formed, maintained and located above the upper aspect of the sample injector tube (2), as described above. Note also that upper aspect of the sample injector tube (2) typically projects to a vertical level very near the upper aspect of the intermediate tube (3). Intermediate tube (3) also tapers (3T), but in an opposite manner to the taper of sample injector tube (2).

While a tapering sample injector tube (2), the upper aspect of which extends to a vertical level just below the top of the intermediate tube (3) of a torch, is a beneficial design for sample flows which contain relatively low sample solids content, said design leads to torch clogging when used with sample flows which contain high sample solids content. High solids content samples are associated with preparation by a highly efficient technique known as Ultrasonic Nebulization. Low solids content samples are typically prepared by low efficiency pneumatic nebulization techniques. While the specifics of the various nebulization techniques are not critical to the subject matter herein, it is important to understand that ultrasonic nebulization provides a sample with a sample solids content upwards of thirty (30) or more times that provided by standard low efficiency sample nebulization techniques.

It should be appreciated that when high efficiency ultrasonic nebulization is utilized, a torch which is resistant to becoming clogged by high sample solids content would be of great utility. With this in mind the present invention is introduced as a High Solids Content Sample Torch. The present invention recognizes that various sample solids which might be introduced into a high solids content sample torch will have various characteristics as regards their propensity to adhere to surface in a torch, and eventually accumulate to the point that the torch is clogged, or to the point that sample solids from one analysis procedure are "carried-over" to a subsequent analysis procedure. In addition, it should be recognized that the design of the torch components will determine, to a large extent, what occurs inside a torch during use. For example, the point at which the sample injector tube (2) tapers (2T)in the standard torch shown in FIG. 1, is a source of clogging problems when high solids content sample flows are introduced thereto.

The present invention identifies three basic considerations, or alternatively phrased, design criteria for torches which are to be used in analysis of high solids content samples. The first is that the sample injection tube should be essentially without critical tapers, or that any tapers present should at least be minimized. The second is that auxiliary gas flow can be used to aid sample movement through a torch, thereby minimizing the possibility that sample solids will condense on, adhere to and accumulate on torch components and eventually clog the torch, or simply remain and later dislodge, thereby contaminating subsequent sample analysis carried out in said torch. This effect is commonly termed "carry-over contamination" or "memory effect" as alluded to above. The third design criteria is based upon the fact that that various sample solids will not adhere to torch components when said torch components are maintained at certain temperatures, or periodically cycled through various temperature regimes, and is utilized via means by which the temperature of various components of a torch can be controlled by introduction of controlled temperature fluid (gas or liquid), flows, or by other temperature control means. A focus in the present invention is to control the temperature of a sample per se, either externally or by way of torch component temperature control. This focus is not taught in any prior reference of which the inventors herein are aware. During use of a high solids content sample torch external contrc' of the "solvent vapor content" present with sample solids can also be adjusted. Typically this is accomplished in the desolvation portion of a nebulizer system by varying the degree of desolvation achieved.

In view of the above, it should be recognized that torch designs which allow for easy flow of a sample per se, and/or which allow use of auxiliary gas flow(s) to aid sample flow, and/or which allow control of the temperature of various components of a torch and sample, would be of great utility when high solids content samples are to be analyzed. In the following, a generic and three modified embodiments of a high solids content sample torches are disclosed. The various embodiments each select and utilize various combinations of the three considerations or design criteria identified above.

Turning now to FIG. 2*a*, there is shown a generic embodiment of a high solids content sample torch (20). As in the case of a standard torch there are present outer (14) and intermediate (13) tubes as well as sample injector tube (12). Also present are an auxiliary jacket tube (15), a barrier tube (11) and an auxiliary injector tube (8). As in the case of the standard torch there are present outer (16) and intermediate (17) ports and a sample flow port (12P). Tangential or vertical gas flows (A) and (B) are entered at outer and intermediate ports (16) and (17) respectively, and sample flow (C) is entered at sample flow port (12P) just as is the case with respect to the analogically similar flows in a standard torch. Also present in the generic embodiment are temperature-in and temperature-out ports (19) and (18) respectively, and auxiliary sample flow port (29). Typically, temperature controlled fluid (eg. gas or liquid) inflow (E) is caused to flow into temperature-in (19) port, through the annular space between the outer surface of the auxilliary injector tube (8) and the inner surface of the barrier tube (11), over the upper aspect of the barrier tube (11) and out of temperature-out port (18) by way of the continuous annular space between the outer surface of the barrier tube (11) and the inner surface of the auxilliary jacket tube (15). Said temperature controlled fluid outflow is designated as (D) in FIG. 2*a*. The purpose of said temperature of the auxiliary injector allow a user to control the temperature of the auxiliary injector tube (8). (Note that the fluid inflow (E) can also be at temperature-out port (18) and fluid outflow (D) can be at temperature-in port (19) and be within the scope of the present invention. The Claims include both possibilities). Also shown in FIG. 2*a* is a gas flow (F) into auxiliary sample flow port (29). Gas flow (F) is caused to flow vertically in the space between the inner surface of the auxiliary injector tube (8) and the outer surface of the sample injector tube (12). Said vertical gas flow (F) mingles with the sample flow (C) at the point where it ejects from the upper aspect of the sample injector tube (12) and vertical gas flow (F) helps the sample flow rise into the upper area (25) of the generic embodiment high solids content sample torch (20) in which a plasma can be created. FIG. 2*b* shows an expanded scale cross sectional view of the generic embodiment of the high solids content sample torch (20), as viewed from above the torch, said cross section being taken at a—a on FIG. 2*a*. FIG. 2*b* aids with visualizing the relationship between the various concentrically oriented tubes of the generic invention. Note also that the vertically upper aspect of sample injector tube (12) typically ends below the vertically upper aspect of the auxiliary injector tube (8). It also is mentioned that sample injector tube (12) can be a permanently affixed component to generic high solids content sample torch (20), or it can be a separate tube which is inserted into the space within the inner surface of auxiliary injector tube (8). In either case, but particularly in the later case, a temperature control element (not shown in FIG. 2*a*, see FIG. 3*b* and discussion thereof below), can be included in sample injector tube (12), such as an high ohmic resistive electrical coil. Said temperature control element, if present, will allow precise control of the temperature of the sample injector tube, and indirectly the sample per se, during use of the generic high solids content sample torch (20).

Turning now to FIG. 3a, there is shown a first modified embodiment of the high solids content sample torch (30). Said first modified embodiment is arrived at by removing some of the components present in the generic embodiment of FIG. 2a. In particular note that outer tube (34) and intermediate tube (33) are present as are outer and intermediate ports indicated by the numerals (36) and (37) respectively in FIG. 3a. Said access ports allow introduction of typically tangential, but optionally vertically (laminar) injected, gas flows (A) and (B), analogous to flows similarly identified in FIG. 2a, into the annular spaces between the inner surface of the outer tube (34) and the outer surface of the intermediate tube (33), and between the inner surface of the intermediate tube (33) and the outer surface of the auxiliary injector tube (38), termed here a support tube based upon its associated function, respectively. Also present is a sample injector tube (32). The other elements of the generic high solids content sample torch (10) of FIG. 2a are removed. Also note that the sample injector tube (32) is not permanently affixed to the other components of the first modified embodiment of the high solids sample torch (30). Instead, said sample injector tube (32) slides into the space within the support tube (38). As a result it is relatively easy to provide a sample injector tube, the vertically upper aspect of which extends to a user selected level with respect to the vertically upper aspect of the support tube (38), and which sample injector tube (32) has incorporated therein a temperature control element (31). FIG. 3b shows a portion of a sample injector tube (32) with a high ohmic resistive electrical coil (31) wrapped therearound. Also shown is a partial view of an optional insulator tube (35), in cross section. Said insulator tube (35) can be used with sample injector tube (32) to protect and insulate said sample infector tube (32). In use a current can be applied to said high ohmic resistive electrical coil to control the temperature of the sample injector tube (32) throughout its entire length. The high ohmic resistance electrical coil (31) can also be placed in the insulator tube (35) if it is present. A functionally equivalent heating element can also be substituted in either the sample injector tube (32) or insulator (35). The sample injector and insulator tubes (32) and (35) respectively, are of a flexible construction, can be easily, removably, inserted into the support tube (38) and positionally adjusted therein.

Turning now to FIG. 4, there is shown a second modified embodiment of the high solids content sample torch (40). It will be appreciated that outer tube (44), intermediate tube (43), auxiliary injector tube (48) and sample injector tube (42) are all arranged generally similar to the analogically equivalent components in FIGS. 2a and 3a, and that outer and intermediate ports (46) and (47) respectively allow the introduction of typically tangential, but optionally injected vertical (laminar) flows (A) and (B) of gas similar to outer and intermediate ports (36) and respectively (37) in FIG. 3a and outer and intermediate ports (16) and (17) respectively in FIG. 2a. Note, however, that in the present case, unlike the embodiment shown in FIG. 3a, sample injector tube (42) is an intricate part of the torch, and that a very definite annular space through which gas can be flowed is present between the inner surface of the auxiliary injector tube (48) and the outer surface of the sample injector tube (42). Auxiliary sample flow port (49) provides access to said annular space similar to the analogically similar port (29) in the generic embodiment of FIG. 2a. Note that it is preferred that the upper aspect of sample injector tube (42) be positioned vertically below the upper aspect of the auxiliary injector tube (48), and that sample injector tube (42) typically not have any tapers present therein. It is within the scope of the invention to extend the upper aspect of the sample injector tube (42) to a higher vertical level, but as shown, in use, a sample flow entered at sample flow port (42P) and ejected from the upper aspect of the sample injector tube (42) will be mixed with the vertical gas flow (F) entered at auxiliary sample flow port (49), which gas flow (F) will aid the sample flow to rise into the upper aspect (44) of the torch (40) in which a plasma can be created and utilized in sample analysis, much as was described for gas flow (F) with respect to FIG. 2a. Said interaction of sample flow (C) and auxiliary gas flow (F) reduces the tendency for sample solids to deposit onto torch (40) components.

Turning now to FIG. 5, there is shown a third modified embodiment (50) of the present invention. Again, the basic components of torch (50) comprising the outer tube (54), intermediate tube (53) and sample injector tube (52) are present and serve purposes similar to analogically similar components described with respect to earlier presented embodiments, (e.g. torches (20) and (40)). Note that the sample injector tube (52) might be slightly tapered at its upper aspect. Also present is an auxiliary jacket tube (55) and barrier tube (51) which are similar to the analogically equivalents (15) and (11) of FIG. 2a and which serve similar purposes thereto. Note that outer and intermediate ports (56) and (57) respectively are present to allow tangential (or vertical), gas flows (A) and (B) respectively to be entered, again for similar purposes to said tangential gas flows (A) and (B) described with respect to earlier presented embodiments. Also note that temperature-in (59) and temperature-out (58) ports are present to allow entry of temperature fluid inflow (E) at temperature-in port (59), which temperature fluid flow exits as temperature fluid outflow (D) at temperature-out port (58). Again, said components and fluid flows are present for similar reasons to those discussed with respect to the analogically similar components described with respect to the generic embodiment of the high solids content sample torch (20) shown in FIG. 2a. In particular it should be understood that control of the temperature of sample flow (C) per se. can be achieved by control of the temperature of the sample injector tube (52). As in the generic embodiment of FIG. 2, fluid inflow (E) can be injected into temperature-out port (18) and flow out of temperature-in port (19) and still be within the scope of the present invention as Claimed. Also present is sample flow port (52P) which allows entry of a sample flow (C).

It is of interest to note that the embodiment (50) of FIG. 5 results from the embodiment (20) of FIG. 2a when the auxiliary injector tube (8) in FIG. 2a is reduced in diameter so that its inner surfaces merges with the outer surface of sample injector tube (12) thereby eliminating the annular space which previously existed therebetween, and as a result, auxiliary sample flow access port (29). As well, the embodiment (40) of FIG. 4 results when the embodiment (20) of FIG. 2a has the auxiliary jacket tube (15), barrier tube (11) and temperature-in and temperature-out access ports (19) and (18) respectively removed therefrom. Similarly, the embodiment (30) of FIG. 3a results from the embodiment (20)

of FIG. 2a when all components thereof except the outer tube (14), intermediate tube (13) and auxiliary injector tube, (termed a support tube is said modified embodiment), (8) are eliminated. Of course, the embodiment of FIG. 3a requires that a separate sample injector tube (32) be provided to the space within the auxiliary injector tube (38) thereof during use.

It is to be understood that wile definite relative port positions are shown consistently in all of the Figures, it is within the scope of the present invention to alter the indicated relative arrangement of the various ports in a manner which retains the associated functional aspects thereof. It is also to be understood that while various upper aspect levels of the sample injector tubes of the various Figures, with respect to upper aspects of the other components of the various embodiments are shown in the various Figures, it is within the scope of the present invention to provide other than the shown relationships. For instance, the upper aspect of sample injector tube (12) in the generic FIG. 2a embodiment (20) might be positioned at a vertical level equal to, or even higher than, the upper aspect of the associated auxiliary injector tube (8). The same consideration applies to the embodiments of the high solids sample torches (30) and (40) shown in FIGS. 3a and 4 respectively.

Having hereby disclosed the subject matter of this invention, it should be obvious that many modifications, substitutions, and variations of the present invention are possible in light of the teachings. It is therefore to be understood that the invention may be practiced other than as specifically described, and should be limited in breadth and scope only by the claims.

We claim:

1. A high solids content sample torch, of the type used in inductively coupled plasma analysis of samples, which high solids content sample torch is resistant to sample carry-over and clogging when a high solids content sample is entered thereto during use, which high solids content sample torch comprises:

a sample injector tube which has a space therethrough, through which space a sample is caused to flow during use, which space is accessible through a sample flow port;

an auxiliary injector tube which concentrically surrounds the sample injector tube, thereby forming an annular space between said sample injector tube and said auxiliary injector tube, through which annular space a sample flow aiding auxiliary gas of a desired temperature can be caused to flow simultaneous with sample flow through the sample injector tube during use, said annular space being accessible through an auxiliary sample flow port;

a barrier tube which concentrically surrounds the auxiliary injector tube thereby forming an annular space between said auxiliary injector tube and said barrier tube, said annular space being accessible through a temperature-in port;

an auxiliary jacket tube which concentrically surrounds the barrier tube, thereby forming an annular space between said barrier tube and the auxiliary jacket tube, said annular space being accessible through a temperature-out port;

which auxiliary jacket tube merges with the auxiliary injector tube beyond the extent of the barrier tube such that a continuous enclosed space exists between the temperature-in and temperature-out ports, along an outer surface length of said auxilliary injector tube, through which a temperature controlled fluid can be caused to flow during use, the purpose thereof being to control the temperature of a simultaneous flow of sample in the sample injector tube and thereby reduce sample adherence to and accumulation in said high solids content sample torch;

an intermediate tube which concentrically surrounds the auxiliary jacket tube, thereby forming an annular space between said auxiliary jacket tube and said intermediate tube, through which annular space a gas can be caused to flow during use, said annular space being accessible through an intermediate port; and an outer tube which concentrically surrounds the intermediate tube, thereby forming an annular space between said intermediate tube and the outer tube, through which annular space a gas can be caused to flow during use, said annular space being accessible through an outer port;

which sample injector, auxiliary injector, barrier, auxiliary jacket, intermediate and outer tubes are each of an elongated shape with a longitudinal dimension, which longitudinal dimensions are typically oriented so as to project essentially vertically during use, the upper aspect of said outer tube being projected to a higher vertical level than the upper aspects of the other identified tubes, thereby providing a space therewithin above the upper aspects of the other tubes in which a plasma is created during use.

2. A high solids content sample torch as in claim 1, in which, during use, the upper aspect of the sample injector tube is at a lower vertical level as compared to the upper aspect of the auxiliary injector tube.

3. A high solids content sample torch as in claim 1, in which the sample injector tube is a removable element.

4. A high solids content sample torch as in claim 1, in which the sample injector tube has temperature control means thereon.

5. A high solids content sample torch of the tape used in inductively coupled plasma analysis of samples, which high solids content sample torch is resistant to sample carry-over and clogging when a high solids content sample is entered thereto during use, which high solids content sample torch comprises:

a sample injector tube which is removable from the high solids content sample torch, which sample injector tube has a space therethrough, through which space a sample is caused to flow during use;

a support tube which concentrically surrounds said sample injector tube, said sample injector tube being positioned in a space through said support tube during use;

an intermediate tube which concentrically surrounds said support tube, thereby forming an annular space between said support tube and intermediate tube, through which annular space tube a gas can be caused to flow during use, said annular space being accessible through an intermediate port;

an outer tube which concentrically surrounds said intermediate tube, thereby forming an annular space between said intermediate tube and outer tube, through which annular space a gas can be caused to flow during use, said annular space being accessible through an outer port;

which sample injector, support, intermediate and outer tubes are each of an elongated shape with a longitudinal dimension, which longitudinal dimensions are typically oriented so as to project essentially vertically during use wherein the sample injector tube includes temperature control means.

6. A high sample solids content torch as in claim 5, in which, during use, the upper aspect of the sample injector tube is at a lower vertical level as compared to the upper level of the support tube.

7. A high solids content sample torch as in claim 5, in which the removable sample injector tube includes temperature control means thereon.

8. A high solids content sample torch as in claim 5, in which the removable sample injector tube is a flexible element removably contained within a flexible insulator with temperature control, means integrated therein.

9. A high solids content sample torch, of the type used in inductively coupled plasma analysis of samples, which high solids content sample torch is resistant to sample carry-over and clogging when a high solids content sample is entered thereto during use, which high solids content sample torch comprises:

a sample injector tube, with a space therethrough, through which space a sample is caused to flow during use, which space is accessible through a sample flow port;

a barrier tube which concentrically surrounds said sample injector tube thereby forming an annular space between said sample injector tube and barrier tube, said annular space being accessible through a temperature-in port;

an auxiliary jacket tube which concentrically surrounds said barrier tube, thereby forming an annular space between said barrier tube and auxiliary jacket tube, said annular space being accessible through a temperature-out port;

which auxiliary jacket tube merges with the sample injector tube at a point beyond the extent of the barrier tube, such that a continuous enclosed space exists between the temperature-in and temperature-out ports, along an outer surface length of said sample injector tube, through which a temperature controlled fluid can be caused to flow during use, the purpose thereof being to control the temperature of a simultaneous flow of sample in the sample injector tube and thereby reduce sample adherence to an accumulation in said high solids content sample torch;

an intermediate tube which concentrically surrounds said auxiliary jacket tube, thereby forming an annular space between said intermediate and auxiliary jacket tube, through which annular space a gas can be caused to flow during use, said annular space being accessible through an intermediate port; and an outer tube which concentrically surrounds said intermediate tube, thereby forming an annular space between said intermediate tube and outer tube, through which annular space a gas can be caused to flow during use, said annular space being accessible through an outer port;

which sample injector, barrier, auxiliary jacket, intermediate and outer tubes are each of an elongated shape with a longitudinal dimension, which longitudinal dimensions are typically oriented so as to project essentially vertically during use, the upper aspect of said outer tube being projected to a higher vertical level than the upper aspects of the other identified tubes, thereby providing a space therewithin above the upper aspects of the other tubes in which a plasma is created during use.

10. A high solids content torch as in claim 9, in which the sample injector tube, at the upper aspect thereof, is slightly tapered inward.

11. A method for analysis of high solids content samples which reduces the tendency for sample solids to adhere to and accumulate upon analysis system components during use, comprising the steps of:

a. obtaining a high solids content sample torch, which high solids content sample torch comprises means for entering a sample thereto and means for controlling the temperature of, said sample thereby causing the sample solids to have a reduced tendency to adhere to and accumulate upon the components of the high solids content sample torch as they flow therethrough;

b. introducing a sample to the high solids content sample torch and causing it to flow therethrough;

c. simultaneously causing the temperature of said sample to be controlled so that sample solids are caused to have a reduced tendency to adhere to and accumulate upon components of the high solids content sample torch; and d. causing the sample solids to be entered into a sample analysis system in which sample analysis is carried out.

12. A method for analysis of high solids content samples which reduces the tendency for sample solids to adhere to and accumulate upon analysis system components during use, comprising the steps of:

a. obtaining a high solids content sample torch, which high solids content sample torch comprises means for entering a sample thereto and means for entering the flow of a temperature controlled auxiliary gas flow thereto so that an entered sample will be aided in its flow through said high solids content sample torch by said temperature controlled auxiliary gas flow and as a result cause the sample solids to have a reduced tendency to adhere to and accumulate upon the components of the high solids content sample torch as it flows therethrough;

b. introducing a sample to the high solids content sample torch and causing it to flow therethrough;

c. simultaneously introducing a temperature controlled auxiliary gas flow to the high solids content sample torch so that sample solids are aided in their flow therethrough and thereby caused to have a reduced tendency to adhere to and accumulate upon components of the high solids content sample torch; and d. causing the sample solids to be entered into a analysis system in which sample analysis is carried out.

13. A method of analysis of high solids content samples which reduces the tendency of sample solids to adhere to and accumulate upon analysis system components during use, comprising the steps of:

a. obtaining a high solids content sample torch, of the type used in inductively coupled plasma analysis of samples, which high solids content sample torch is resistant to sample carry-over and clogging when a high solids content sample is entered thereto during use, which high solids content sample torch comprises:

a sample injector tube with a space therethrough, through which space a sample is caused to flow during use, which space is accessible through a sample flow port, which sample injector tube can be removable from the high solids content sample torch;

an auxiliary injector tube which concentrically surrounds the sample injector tube, thereby forming an annular space between said sample injector tube and said auxiliary injector tube, through which annular space a sample flow aiding auxiliary gas of a desired temperature can be, simultaneous with sample flow through the sample injector tube, caused to flow during use, said annular space being accessible through an auxiliary sample flow port, which auxilliary injector tube can be removable from said high solids content sample torch;

an intermediate tube which concentrically surrounds the auxiliary injector tube, thereby forming an annular space between said auxiliary injector tube and said intermediate tube, through which annular space a gas can be caused to flow during use, said annular space being accessible through an intermediate port; and an outer tube which concentrically surrounds the intermediate tube, thereby forming an annular space between said intermediate tube and the outer tube, through which annular space a gas can be caused to flow during use, said annular space being accessible through an outer port;

which sample injector, auxiliary injector, intermediate and outer tubes are each of an elongated shape with a longitudinal dimension, which longitudinal dimensions are oriented so as to project essentially vertically during use;

the primary purpose of said sample and auxiliary gas flows being to provide sample to the upper aspect of the high solids content sample torch, in a manner which reduces the propensity of sample solids to adhere to and accumulate upon components of the high solids content sample torch, at which upper aspect thereof a plasma can be created and whereat said sample and plasma can interact and produce sample identifying products which can be analyzed, and a second purpose of said auxiliary gas flow being to allow a user of the high solids content sample to control the temperature of the sample injector tube and sample flowing therein by controlling the temperature of the auxiliary gas flow, to further control and reduce the propensity of sample solids to adhere to and accumulate on the high solids content sample torch components; and the primary purpose of said gas flows typically entered at the intermediate and outer ports being to shield the components of the high solids content sample torches contacted thereby from the temperatures created in the plasma; but which gas flow entered at the intermediate port in particular, also serves to aid with plasma positioning in said high solids content sample torch;

b. entering a sample flow to the sample flow port;

c. simultaneously entering an auxiliary gas flow of a desired temperature to the auxiliary sample flow port;

d. typically entering gas flows to the outer and intermediate ports;

such that the sample flow is aided in its passage through said high solids content sample torch by a reduced tendency of sample solids to adhere to and accumulate upon components of said high sample solids content torch.

14. A method for analysis of high solids content samples, as in claim 13, which further comprises the step of controlling the temperature and solvent vapor content of the sample external to the torch.

15. A method for analysis of high solids content samples as in claim 13 which further comprises the steps of adjusting the location of the upper aspect of the sample injector tube within the auxiliary injector tube.

16. A method for analysis of high solids content samples which reduces the tendency of sample solids to adhere to and accumulate upon analysis system components during use, comprising the steps of:

a. obtaining a high solids content sample torch, of the type used in inductively coupled plasma analysis of samples, which high solids content sample torch is resistant to sample carry-over and clogging when a high solids content sample is entered thereto during use, which high solids content sample torch comprises:

a sample injector tube with a space therethrough, through which space a sample is caused to flow during use, which space is accessible through a sample flow port, which sample injector tube can be removable from the high solids content sample torch;

an auxiliary injector tube which concentrically surrounds the sample injector tube, thereby forming an annular space between said sample injector tube and said auxiliary injector tube, through which annular space a sample flow aiding auxiliary gas flow of a desired temperature can be caused to flow simultaneous with sample flow through the sample injector tube during use, said annular space being accessible through an auxiliary sample flow port;

a barrier tube which concentrically surrounds the auxiliary injector tube thereby forming an annular space between said auxiliary injector tube and said barrier tube, said annular space being accessibly through a temperature-in port;

an auxiliary jacket tube which concentrically surrounds the barrier tube, thereby forming an annular space between said barrier tube and the auxiliary jacket tube, said annular space being accessible through a temperature-out port;

which auxiliary jacket tube merges with the auxilliary injector tube beyond the extent of the barrier tube such that a continuous enclosed space exists between the temperature-in and temperature-out ports, along an outer surface length of said auxilliary injector tube, through which a temperature controlled fluid can be caused to flow during use, the purpose thereof being to control the temperature of a simultaneous flow of sample in the sample injector tube and thereby reduce sample adherence to and ₄ccumulation in said high solids content sample torch;

an intermediate tube which concentrically surrounds the auxiliary jacket tube, thereby forming an annular space between said auxiliary jacket tube and said intermediate tube, through which annular space a gas can be caused to flow during use, said annular space being accessible through an intermediate port; and an outer tube which concentrically surrounds the intermediate tube, thereby forming an annular space between said intermediate tube and the outer tube, through which annular space a gas can be caused to flow during use, said annular space being accessible through an outer port;

which sample injector, auxiliary injector, barrier, auxiliary jacket, intermediate and outer tubes are each of an elongated shape with a longitudinal dimension, which longitudinal dimensions are typically oriented so as to project essentially vertically during use, the upper aspect of said outer tube being projected to a higher vertical level than the upper aspects of the other identified tubes, thereby providing a space therewithin above the upper aspects of the other tubes in which a plasma can be formed during use;

the primary purpose of said sample and auxiliary gas flows being to provide sample to the upper aspect of the high solids content sample torch, in a manner which reduces the propensity of sample solids to adhere to and accumulate upon components of the high solids content sample torch, at which upper aspect thereof a plasma can be created and whereat said sample and plasma can interact and produce sample identifying products which can be analyzed, and a second purpose of said auxiliary gas flow being to allow a user of the high solids content sample to control the temperature of the auxiliary injector tube by controlling the temperature of the auxiliary gas flow, to further control and reduce the propensity of sample solids to adhere to and accumulate on the high solids content sample torch components;

the primary purpose of said temperature controlled fluid flow being to allow a user of the high solids content sample torch to control the temperature of the components thereof contacted by said temperature controlled fluid flow, and indirectly the temperature of the sample present in the sample injector tube, thereby reducing the propensity for sample solids to adhere to and accumulate on said components; and the primary purpose of said gas flows typically entered at the intermediate and outer ports being to shield the components of the high solids content sample torches contacted thereby from the temperatures created in the plasma; but which gas flow entered at the intermediate port in particular, also serves to aid with plasma positioning in said high solids content sample torch;

b. entering a flow of sample to the sample flow port;

c. optionally entering a temperature controlled fluid flow to the temperature-in or temperature-out port and causing it to exit at the temperature-out or temperature-in port respectively;

d. typically entering gas flows to the intermediate and outer ports;

such that sample flow is aided in its passage through said high solids content sample torch by a reduced tendency of said sample solids to adhere to and accumulate upon components of the high solids content sample torch.

17. A method for analysis of high solids content samples as in claim 16 which further comprises the step of entering an auxiliary gas flow of a desired temperature into the auxiliary sample flow port.

18. A method for analysis of high solids content samples, as in claim 17 which further comprises the step of controlling the temperature and solvent vapor content of the sample external to the torch.

19. A method for analysis of high solids content samples, as in claim 16 which further comprises the step of controlling the temperature and solvent vapor content of the sample external to the torch.

20. A method for analysis of high solids content samples as in claim 16, which further comprises the steps of adjusting the location of the upper aspect of the sample injector tube within the auxiliary injector tube.

21. A method of analysis of high solids content samples which reduces the tendency of sample solids to adhere to and accumulate upon analysis system components during use, comprising the steps of:

a. obtaining a high solids content sample torch of the type used in inductively coupled plasma analysis of samples, which high solids content sample torch is resistant to sample carry-over and clogging when a high solids content sample is entered thereto, which high solids content sample torch comprises:

a sample injector tube which is removable from said high solids content sample torch and optionally includes temperature control means thereon, which sample injector tube has a space therethrough, through which space a sample is caused to flow during use;

a support tube which concentrically surrounds said sample injector tube, said sample injector tube being positioned in a space through said support tube during use;

an intermediate tube which concentrically surrounds said support tube, thereby forming an annular space between said support tube and intermediate tube, through which annular space a gas can be caused to flow during use, said annular space being accessible through an intermediate port;

an outer tube which concentrically surrounds said intermediate tube, thereby forming an annular space between said intermediate tube and outer tube, through which annular space a gas can be caused to flow during use, said annular space being accessible through an outer port;

which sample injector, support, intermediate and outer tubes are each of an elongated shape with a longitudinal dimension, which longitudinal dimensions are typically oriented so as to project essentially vertically during use;

the primary purpose of said sample flow being to provide sample to the vertically upper aspects of the high solids content sample torch, in a manner which reduces the propensity of the sample solids to adhere to and accumulate on components of the high solids content sample torch, at which upper aspect thereof a plasma can be created and whereat said sample and plasma can interact and produce sample identifying products which can be analyzed, the primary purpose of said gas flows typically entered at the intermediate and outer ports being to shield the components of the high solids content sample torch contacted thereby from the temperatures created in the plasma, but which gas flow typically entered at the intermediate port in particular, also serves to position the plasma in said high solids content sample torch;

b. entering a sample flow to the sample injector tube;

c. optionally controlling the temperature of the sample injector tube by use of temperature control means thereon.

d. typically entering gas flows to the intermediate and outer ports;

such that sample flow is aided in its passage through said high solids content sample torch by a reduced tendency of said sample solids to adhere to and accumulate upon components of the high solids content sample torch.

22. A method for analysis of high solids content samples, as in claim 21, which further comprises the step of controlling the temperature and solvent vapor content of the sample external to the torch.

23. A method for analysis of high solids content samples as in claim 22, which further comprises the steps of adjusting the location of the upper aspect of the sample injector tube within the support tube.

24. A method of analysis of high solids content samples which reduces the tendency of sample solids to adhere to and accumulate upon analysis system components during use, comprising the steps of:
   a. obtaining a high solids content sample torch, of the type used in inductively coupled plasma analysis of samples, which high solids content sample torch is resistant to sample carry-over and clogging when a high solids content sample is entered thereto during use, which high solids content sample torch comprises:

a sample injector tube, with a space therethrough, through which space a sample is caused to flow during use, said space being accessible through a sample flow port;

a barrier tube which concentrically surrounds said sample injector tube, thereby forming an annular space between said sample injector tube and barrier tube, said annular space being accessible through a temperature-in port;

an auxiliary jacket tube which concentrically surrounds said barrier tube, thereby forming an annular space between said barrier tube and auxiliary jacket tube, said annular space being accessible through a temperature-out port;

which auxiliary jacket tube merges with the sample injector tube at a point beyond the extent of the barrier tube, such that a continuous enclosed space exists between the temperature-in and temperature-out ports, along an outer surface length of said sample injector tube, through which a temperature controlled fluid can be caused to flow during use, the purpose thereof being to control the temperature of a simultaneous flow of sample in the sample injector tube and thereby reduce sample adherence to and accumulation in said high solids content sample torch;

an intermediate tube which concentrically surrounds said auxiliary jacket tube, thereby forming an annular space between said intermediate tube and auxiliary jacket tube, through which annular space a gas can be caused to flow during use, said annular space being accessible through an intermediate port; and an outer tube which concentrically surrounds said intermediate tube, thereby forming an annular space between said intermediate tube and outer tube, through which annular space a gas can be caused to flow during use, said annular space being accessible through an outer port;

which sample injector, barrier, auxiliary jacket, intermediate and outer tubes are each of an elongated shape with a longitudinal dimension, which longitudinal dimensions are typically oriented so as to project essentially vertically during use, the upper aspect of said outer tube being projected to a higher vertical level than the upper aspects of the other identified tubes, thereby providing a space therewithin above the upper aspects of the other tubes in which a plasma can be formed during use;

the primary purpose of said sample flow being to provide sample to the vertically upper aspect of the high solids content sample torch, in a manner which reduces the propensity of sample solids to adhere to and accumulate on components of the high solids content sample torch, at which vertically upper aspect thereof a plasma can be created and whereat said sample and plasma can interact and produce sample identifying products which can be analyzed;

the primary purpose of said temperature controlled fluid flow being to allow a user of a high solids content sample torch to control the temperature of the components thereof contacted, and of the sample flowing in the sample injector tube, thereby further controlling the propensity of sample solids to adhere to and accumulate on the high solids sample torch components; and the primary purpose of said gas flows typically entered at the intermediate and outer ports being to shield the components of the high solids content sample torches contacted thereby from the temperatures created in the plasma; but which gas flow entered at the intermediate port in particular, also serves position the plasma in said high solids content sample torch;

b. entering a flow of sample to the sample flow port;
   c. simultaneously entering a temperature controlled fluid flow to the temperature-in or temperature-out port and causing it to exit at the temperature-out or temperature-in port respectively;
   d. typically entering gas flows to the intermediate and outer ports;

such that sample flow is aided in its passage through said high solids content sample torch by a reduced tendency of said sample to adhere to and accumulate on components of the high solids content sample torch.

25. A method for analysis of high solids content samples, as in claim 24 which further comprises the step of controlling the temperature and solvent vapor content of the sample external to the torch.

26. A high solids content sample torch of the type used in inductively coupled plasma analysis of samples, including a sample injector tube, in which the improvement comprises an annular space which concentrically encompasses said sample injector tube, through which annular space a fluid of a desired temperature is caused to flow during use, the purpose thereof being to aid sample, which is simultaneously entered to said sample injector tube, to flow through said sample injector tube, by reducing the tendency of said sample to adhere to and accumulate in said high solids content sample torch; said annular space being other than that formed by an intermediate tube or outer tube which when present concentrically encompass said sample injector tube and said annular space which concentrically encompasses said sample injector tube.

27. A high solids content sample torch, of the type used in inductively coupled plasma analysis of samples, which high solids content sample torch is resistant to sample carry-over and clogging when a high solids content sample is entered thereto during use, which high solids content sample torch comprises:
- a sample injector tube which has a space therethrough, through which space a sample is caused to flow during use, which space is accessible through a sample flow port;
- an auxiliary injector tube which concentrically surrounds the sample injector tube, thereby forming an annular space between said sample injector tube and said auxiliary injector tube, through which annular space a sample flow aiding auxiliary gas of a desired temperature can be caused to flow simultaneous with sample flow through the sample injector tube during use, said annular space being accessible through an auxiliary sample flow port;
- a barrier tube which concentrically surrounds the auxiliary injector tube thereby forming an annular space between said auxiliary injector tube and said barrier tube, said annular space being accessible through a temperature-in port;
- an auxiliary jacket tube which concentrically surrounds the barrier tube, thereby forming an annular space between said barrier tube and the auxiliary jacket tube, said annular space being accessible through a temperature-out port;
- which auxiliary jacket tube merges with the auxiliary injector tube beyond the extent of the barrier tube such that a continuous enclosed space exists between the temperature-in and temperature-out ports, along an outer surface length of said auxilliary injector tube, through which a temperature controlled fluid can be caused to flow during use, the purpose thereof being to control the temperature of a simultaneous flow of sample in the sample injector tube and thereby reduce sample adherence to and accumulation in said high solids content sample torch;
- an outer tube which concentrically surrounds the auxiliary jacket tube, thereby forming an annular space between said auxiliary jacket tube and said outer tube, through which annular space a gas can be caused to flow during use, said annular space being accessible through an outer port; and
- which sample injector, auxiliary injector, barrier, auxiliary jacket, and outer tubes are each of an elongated shape with a longitudinal dimension, which longitudinal dimensions are typically use, the upper aspect of said outer tube being projected to a higher vertical level than the upper aspects of the other identified tubes, thereby providing a space therewithin above the upper aspects of the other tubes in which a plasma is created during use.

28. A high solids content sample torch, of the type used in inductively coupled plasma analysis of samples, which high solids content sample torch is resistant to sample carry-over and clogging when a high solids content sample is entered thereto during use, which high solids content sample torch comprises:
- a sample injector tube, with a space therethrough, through which space a sample is caused to flow during use, which space is accessible through a sample flow port;
- a barrier tube which concentrically surrounds said sample injector tube thereby forming an annular space between said sample injector tube and barrier tube, said annular space being accessible through a temperature-in port;
- an auxiliary jacket tube which concentrically surrounds said barrier tube, thereby forming an annular space between said barrier tube and auxiliary jacket tube, said annular space being accessible through a temperature-out port;
- which auxiliary jacket tube merges with the sample injector tube at a point beyond the extent of the barrier tube, such that a continuous enclosed space exists between the temperature-in and temperature-out ports, along an outer surface length of said sample injector tube, through which a temperature controlled fluid can be caused to flow during use, the purpose thereof being to control the temperature of a simultaneous flow of sample in the sample injector tube and thereby reduce sample adherence to and accumulation in said high solids content sample torch;
- an outer tube which concentrically surrounds said auxiliary jacket tube, thereby forming an annular space between said auxiliary jacket tube and outer tube, through which annular space a gas can be caused to flow during use, said annular space being accessible through an outer port; and
- which sample injector, barrier, auxiliary jacket and outer tubes are each of an elongated shape with a longitudinal dimension, which longitudinal dimensions are typically oriented so as to project essentially vertically during use, the upper aspect of said outer tube being projected to a higher vertical level than the upper aspects of the other identified tubes, thereby providing a space therewithin above the upper aspects of thereby providing a space therewithin above the upper aspects of the other tubes in which a plasma is created during use.

* * * * *